United States Patent [19]

Ouriel et al.

[11] Patent Number: 4,846,800
[45] Date of Patent: Jul. 11, 1989

[54] TWO CHAMBERED AUTOTRANSFUSER DEVICE AND METHOD OF USE

[76] Inventors: Kenneth Ouriel, 32 Pickford Dr., Rochester, N.Y. 14618; Karl D. (Skip) Kirk, III, 104 Bedford St., New York, N.Y. 10014; Douglas M. Spranger, 142 E. 37th St., New York, N.Y. 10016

[21] Appl. No.: 108,397

[22] Filed: Oct. 14, 1987

[51] Int. Cl.⁴ .............................................. A61M 37/00
[52] U.S. Cl. ........................................ 60.4/4; 417/122; 604/319
[58] Field of Search .............. 417/122, 149; 604/319, 604/335, 4

[56] References Cited

U.S. PATENT DOCUMENTS

| | | | |
|---|---|---|---|
| 1,886,818 | 11/1932 | Kipp | 417/149 X |
| 3,216,419 | 11/1965 | Scislowicz | 128/214 |
| 3,492,991 | 2/1970 | Dyer, Jr. | 128/214 |
| 3,507,395 | 4/1970 | Bentley | 210/443 |
| 3,585,995 | 6/1971 | Perkins et al. | 128/214 |
| 3,625,211 | 12/1971 | Butler | 128/214 C |
| 3,730,647 | 5/1973 | Lonardo | 417/149 X |
| 3,896,733 | 7/1975 | Rosenberg | 128/214 R |
| 3,965,896 | 6/1976 | Swank | 128/214 R |
| 3,989,043 | 11/1976 | Dimeff | 128/214 C |
| 4,006,745 | 2/1977 | Sorenson et al. | 128/214 R |
| 4,014,329 | 3/1977 | Welch et al. | 128/214 R |
| 4,033,345 | 7/1977 | Sorenson et al. | 128/214 R |
| 4,047,526 | 9/1977 | Reynolds et al. | 128/214 R |
| 4,078,563 | 3/1978 | Tuseth | 128/214 C |
| 4,173,222 | 11/1979 | Muetterties | 128/214 C |
| 4,177,808 | 12/1979 | Malbec | 128/214 R |
| 4,424,053 | 1/1984 | Kurtz et al. | 604/4 |
| 4,443,220 | 4/1984 | Hauer et al. | 604/408 |
| 4,466,888 | 8/1984 | Verkaart | 210/232 |
| 4,500,308 | 2/1985 | Kurtz et al. | 604/4 |
| 4,501,581 | 2/1985 | Kurtz et al. | 604/52 |
| 4,540,406 | 9/1985 | Miles | 604/269 |
| 4,551,131 | 11/1985 | Miles et al. | 604/31 |
| 4,564,359 | 1/1986 | Ruhland | 604/4 |
| 4,568,367 | 2/1986 | Gremel et al. | 55/178 |
| 4,573,992 | 3/1986 | Marx | 604/408 |
| 4,631,050 | 12/1986 | Reed et al. | 604/4 |
| 4,642,088 | 2/1987 | Gunter | 604/4 |
| 4,642,089 | 2/1987 | Zupkas et al. | 604/4 |
| 4,655,740 | 4/1987 | Ruhland | 604/4 |
| 4,657,529 | 4/1987 | Prince et al. | 604/6 |

OTHER PUBLICATIONS

Dyer, Jr., "Intraoperative Autotransfusion: a Preliminary Report and New Method", *American Journal of Surgery*, vol. 112, Dec. 1966, pp. 874-878.

Primary Examiner—William E. Wayner
Attorney, Agent, or Firm—Kenyon & Kenyon

[57] ABSTRACT

An autotransfuser includes, in a single receptacle, a pair of chambers separated by a common wall. Each receptacle can alternately perform a blood infusion or blood collection function. Each chamber includes at least three inlets/outlets, a blood inlet, a blood outlet and an air inlet. In some embodiments of the invention the air inlet serves alternately to couple either an air or a pressure source on the one hand or a vacuum source on the other hand to the corresponding chamber. In other embodiments of the invention, the air inlet comprises a vacuum inlet and a separate air or pressure inlet. A disk like device or valve manifold is arranged for rotatable movement adjacent the inlets/outlets. The disk like device includes four channels, one for each of air or pressure, vacuum, blood inlet and blood infusion. Each channel includes a port for coupling to external tubing and at least one channel end. The channel ends are located in the disk like device so that by rotating the disk like device to two distinct positions, one or the other of the functions can be performed by each chamber. A robust blood valve is also disclosed which has a float element of density to allow it to float in a pool of human blood and a significant closure force of about ten grams.

29 Claims, 11 Drawing Sheets

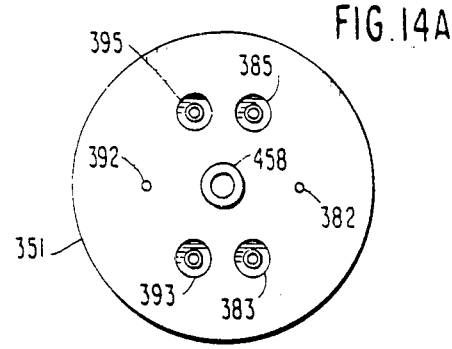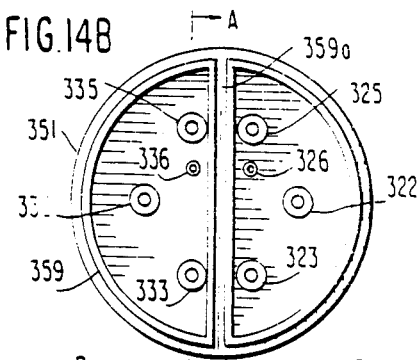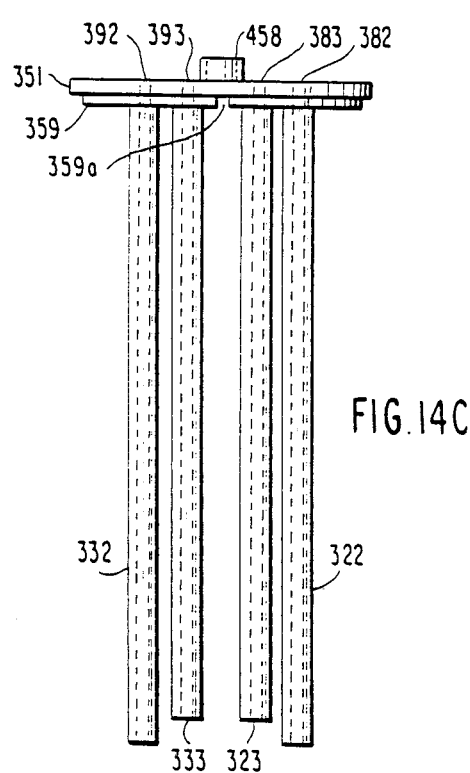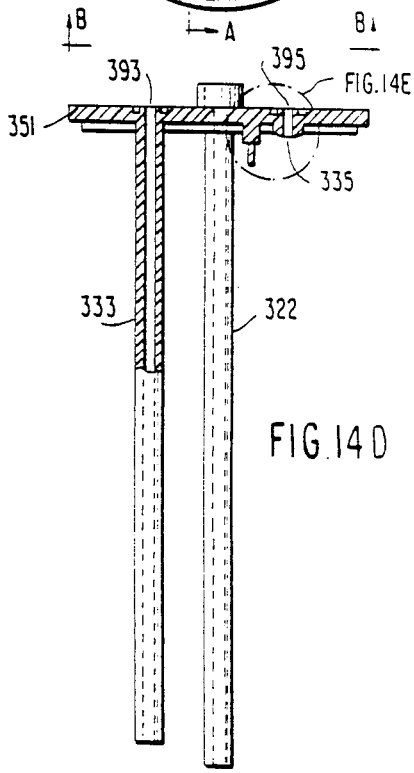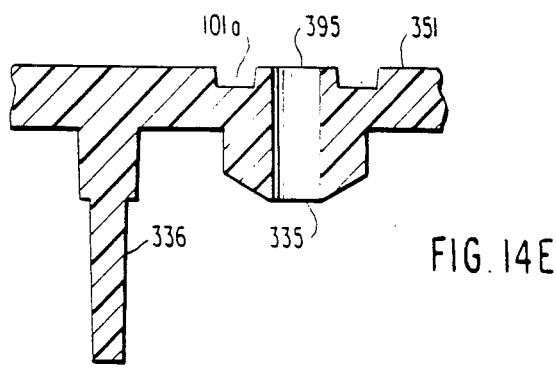

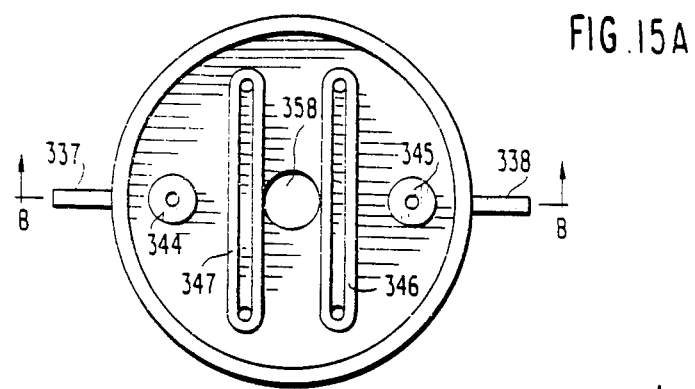
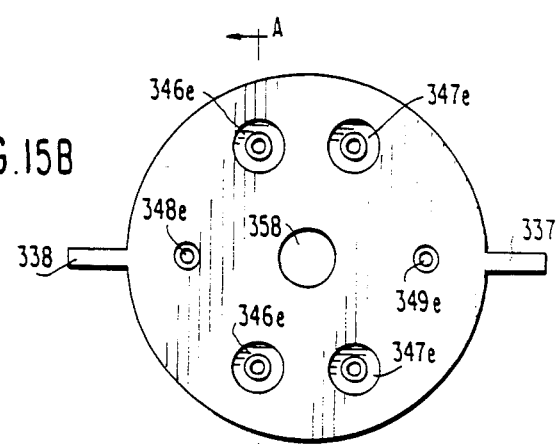
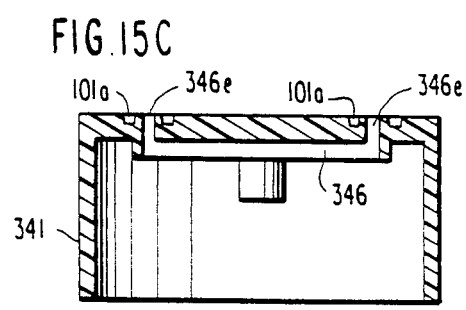
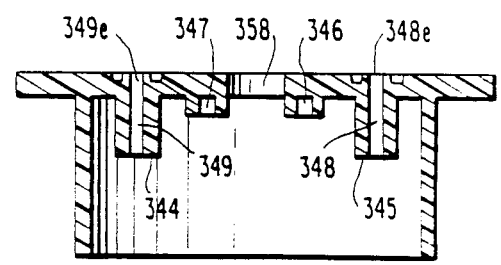
FIG.15A
FIG.15B
FIG.15C
FIG.15D

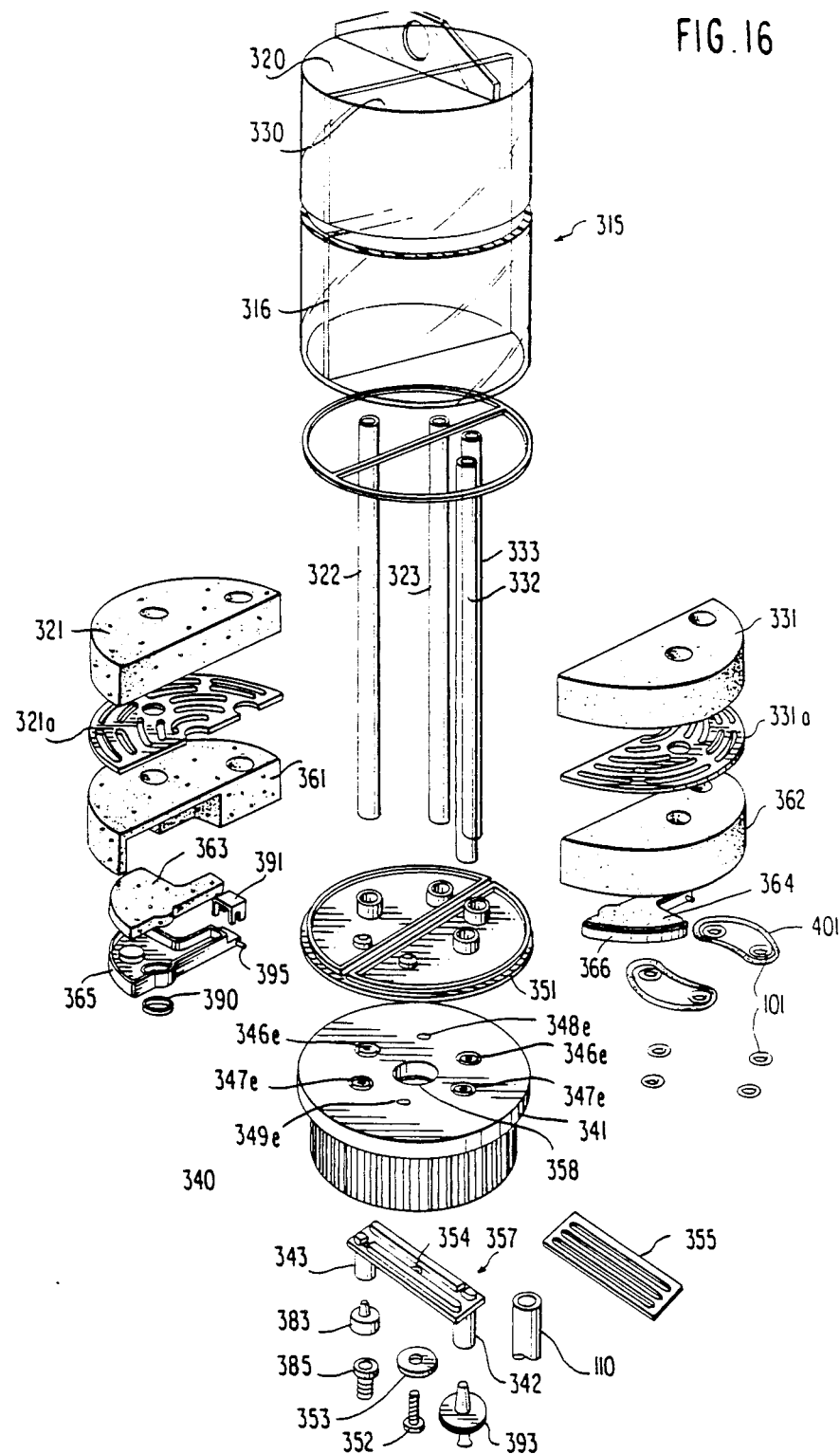

TWO CHAMBERED AUTOTRANSFUSER DEVICE AND METHOD OF USE

DESCRIPTION

1. Field of the Invention

The present invention relates to an autotransfuser particularly adapted for collecting and reinfusing blood lost by a patient during surgery or the like.

2. Background Art

The invention relates to a method and apparatus for autotransfusion of a patient's blood which has been shed during the course of a surgical procedure. Reinfusing a patient's own (autogenous) blood has many advantages over the use of banked blood. The use of autogenous blood minimizes the risk of transmission of Acquired Immunodeficiency Syndrome (AIDS) and transfusion hepatitis. Autotransfusion may minimize the monetary costs associated with transfusing banked blood. Transfusion of bank blood may result in immunologic reactions to foreign proteins, a phenomenon which does not occur with autogenous blood.

Autotransfusion, as a procedure, has not been novel for some time. Duncan described the reinfusion of a patient's own blood after a crush injury to the legs from a railway accident (Duncan J.: On Reinfusion of Blood in Primary and other Amputations. Br. Med. J. 1:192, 1886). Duncan collected the blood in a dish c.ntaoining soda phosphate and then reinfused the blood into the patient. Since the time of Duncan, many autotransfusion systems have been devised. The Bentley pump (Raines J., Buth J., Brewster D. C., Darling R. C.: Intraoperative Autotransfusion. Equipment, Protocols, and Guidelines. J. Trauma 16:616–23, 1976) utilizes a roller pump to aspirate blood into a collection reservoir (Benley Laboratories, Inc., Irving, CA). The Sorensen unit (Noon G. P., Solis R. T., Natelson E. A.: A Simple Method of Intraoperative Autotransfusion. Surgery, Gynecology and Obstetrics 143:65–70. 1976) requires a special suction tip which mixe with the blood (Sorensen Research Corp., Salt Lake City, UT). The New York Times (Business Technology—Sept. 16, 1987) has reported a danger in autotransfusion caused by injecting bubbles or other impurities into the patient's bloodstream.

These and other device are also describe in the patent literature; see: Dyer U.S. Pat. No. 3,492,991; Perkins U.S. Pat. No. 3,585,995; Rosenberg U.S. Pat. No. 3,896,733; Swank U.S. Pat. No. 3,965,896; Sorenson U.S. Pat. Nos. 4,006,745 and 4,033,345; Welch U.S. Pat. No. 4,014,329; Reynolds U.S. Pat. No. 4,047,526; Kurtz U.S. Pat. Nos. 4,424,053, 4,500,308 and 4,501,581; Hauer U.S. Pat. No. 4,443,220; VerKaart U.S. Pat. No. 4,466,888; Miles U.S. Pat. Nos. 4,540,406 and 4,551,131; Ruhland U.S. Pat. Nos. 4,564,359 and 4,655,740; Marx U.S. Pat. No. 4,573,992; Reed U.S. Pat. No. 4,631,050 and Gunter U.S. Pat. No. 4,642,088.

In general, the prior art devices are relatively complex, which is a disadvantage from the point of view of manufacture and use. In terms of usage, complexity necessitates the presence of a specialized technician, which carries unfavorable cost implications. Likewise, from the point of view of manufacturing, complexity also carries unfavorable cost implications. At least some prior art devices are considered dangerous.

Therefore it is an object of the invention to provide an autotransfuser which is both simple and inexpensive to manufacture and, at the same time, simple and inexpensive to use.

It is another object to provide a device which is efficient, controlling the flow of blood to the patient, to reduce the risk to the patient.

SUMMARY OF THE INVENTION

The invention overcomes these and other problems in the prior art and provides an autotransfuser which is simple, low in cost, easy to use and reduces patient risks.

The major components of the autotransfuser include a twochambered receptacle, each chamber of the receptacle can perform both blood collection and blood infusion functions, and typically the function performed by each chamber alternates. Accordingly, while one chamber is collecting blood shed by the patient during the course of the surgical procedure, the other chamber may be a source of previously collected blood which is infused back to the patient. To perform both functions, each chamber includes a blood inlet, a blood outlet and air inlet means including at least one air inlet. In one embodiment of the invention, the air inlet means comprises a vacuum inlet and a separate pressure inlet or vent. In a second embodiment of the invention, a single air inlet alternately performs the function of a vacuum inlet and a pressure inlet or vent, at separate times. The two chambers are defined within a cylindrical receptacle by an interior wall which is common to both the chambers. A rotatable disk like device (akin to a valve manifold) is operatively associated with the receptacle and is rotatable relative thereto. The disk like device includes a plurality of channels including a blood inlet channel, a blood outlet channel, a vacuum channel and a pressure or vent channel. The disk like device includes a port for each channel (for connection to external tubing), each channel also includes at least one channel end. When one of the chambers, for example the chamber we will refer to as chamber A, is performing a blood collection function, a blood inlet channel end coordinates in space with the blood inlet for chamber A, and simultaneously a vacuum channel end coordinates in space with either the single air inlet of chamber A (in one embodiment) or the vacuum inlet for chamber A (in another embodiment). With the disk device in this position, there is, in addition, selective coordination between other channel ends and components of chamber B. More particularly, chamber B at this time may be performing a blood infusion function and to this end a blood outlet of chamber B coordinates in space with an end of the blood outlet channel and at the same time a pressure or vent channel end coordinates in space with either a single air inlet of chamber B (in one embodiment) or a pressure or vent inlet for chamber B (in another embodiment). The channel ends which do not coordinate in space with inlets or outlets are effectively sealed by an adjacent surface of the receptacle.

The disk like device includes four ports, each associated with one of the channels such that there is a blood inlet port associated with the blood inlet channel, a blood outlet port associated with the blood outlet channel, a pressure or vent port associated with the pressure or vent channel and a vacuum port associated with the vacuum channel.

The vacuum port may be attached via conventional tubing to a vacuum source which is conventionally available in surgical theaters. The pressure or vent port of the disk like device is also connected via conventional tubing to any suitable (continuous or intermittent)

pressure source such as a hand-held pressure bulb which can be manually pressurized by an anesthesiologist or an assistant to provide a source of pressure to drive the blood infusion function. Alternatively, the pressure source may be dispensed with and the vent port is merely vented to atmospheric conditions. The blood inlet channel is associated with the blood inlet port which is connected via conventional tubing to a conventional blood aspirating wand which may be manually directed to aspirate the blood shed by the patient during the course of the surgical procedure.

The disk like device, inasmuch as it is rotatable relative to the receptacle, can be rotated from the operative position which has just been described to a different operative position wherein the functions of chambers A and B are reversed, e.g. chamber B becomes a blood collection chamber and chamber A becomes a blood infusion chamber. The disk like device also has at least one off position which results in sealing all channel ends. The disk like device includes a plurality of seals, such as 0-rings adjacent the various channel ends so as to provide air tight coupling between the channel end and an associated inlet or outlet of the chamber when they are coordinated in space. The seals also seal off a channel end which does not coordinate in space with an inlet or outlet of a receptacle. Where necessary seals also seal the chamber inlets and outlets when they do not coordinate in space with a channel end.

In use, the receptacle is maintained in a position wherein a cylindrical axis is generally vertical, so the receptacle has a top and a bottom. In the first and second embodiments the disk-like device is located adjacent the top, but in a preferred embodiment the disk-like device is located adjacent the bottom of the receptacle.

In the first and second embodiments, each chamber includes a valved outlet which is coupled, via piping internal to the receptacle, to the blood outlet. More particularly, to facilitate cooperation between the chamber and the disk like device, the inlets and outlets of the chamber are located in a first wall of the chamber, and the first walls of both chambers are coplanar with each other. On the other hand, the valved outlet of each chamber is located in another wall of the chamber, the other wall is parallel to and spaced from the first wall; in typical use the first walls correspond to the "top" of the chambers whereas the other wall corresponds to the bottom. The bottom of both of the chambers is slightly above the bottom of the receptacle, and the valved outlet is located in between. Thus the piping extends between the outlet side of the valve and the blood outlet. A simple float (which may be hinged to pivot as the fluid level rises and falls) is located within the chamber, and above the valve outlet so as to prevent the escape of air or other gas. The inlet side of this valve may include a strainer.

In the preferred embodiment the disk-like device is adjacent the bottom of the receptacle. Accordingly, the valved outlets (in the bottom of the chambers) are adjacent the disk-like device and the piping internal to the chambers for blood infusion is unnecessary. On the other hand, piping internal to the chambers is required for the air inlet means (either one pipe for pressure or vent and vacuum, or a pipe for pressure or vent and a separate pipe for vacuum) and another for the blood collection function.

An important advantage of the preferred embodiment follows from the position of the disk like device at the bottom of the receptacle. With this arrangement (contrary to the other two embodiments) infusion may be driven entirely by gravity, i.e. the pressure source is no longer essential to the infusion function. Even where the pressure source is not required, it may be present so the operator may speed infusion by pressurizing the chamber. Eliminating the pressure source does not render the pressure channel in the disk like device unnecessary. Even without the pressure source, what was the pressure channel is now a vent channel so that the chamber may be vented to atmospheric pressure to prevent vacuum formation in the infusion chamber which would tend to impede infusion.

In order to facilitate operation and maintain foreign particles from contaminating the blood being transfused, a 0.2 micron filter may be used in the air line that is between the pressure bulb or vent and the pressure port on the disk like device. Furthermore, a 260 micron gross filter may be inserted in the tubing between aspirating wand and the blood inlet port. Finally, a 40 micron microaggregate filter may be used in the tubing a blood outlet port of the disk like device.

The autotransfuser also includes a mounting arrangement for supporting the autotransfuser at a convenient altitude relative to the surgical procedure. The altitude is selected so as to minimize the length of tubing required between the aspirating wand and the blood inlet port and between the blood outlet port and the infusion site.

After the infusion site is prepared, e.g. connection of the tubing between the blood outlet port and the patient's intravenous catheter and the vacuum port is connected via the tubing to a vacuum source, shed blood can be collected by manipulating the handle of the aspirating wand. Prior to actually collecting blood, however, a suitable amount of anticoagulant such as a citrate dextrose solution (ACD) is introduced (such as by aspiration, for example) into the blood collection chamber, e.g. chamber A. Thereafter blood is aspirated and when the chamber becomes full the disk like device is rotated from the position in which blood is collected into chamber A to another operative position wherein blood is collected in chamber B. Because of the spatial arrangement already described, with the disk like device in the second position, chamber A becomes a blood infusion chamber. However, before actually collecting blood in chamber B, ACD or the like is introduced into the second chamber. The anesthesiologist or assistant can control blood infusion or the rate of infusion by manipulating the pressure bulb. When the second chamber is full, the disk like device is again rotated to its first position, ACD is again inserted in the first chamber and the process is repeated.

A distinct difference between the present invention and many of the prior art devices is the manner in which the receptacle is employed. In many of the prior art devices the prior art autotransfuser is used for only a single fill/discharge cycle. Once the prior art autotransfuser is emptied, it is discarded and a fresh (unused) autotransfuser may be used to continue the same procedure. This is distinctly different from the way in which the autotransfuser of the present invention is to be employed. Although the autotransfuser of this invention is contemplated to be disposable, each chamber may undergo several fill/discharge cycles before it is disposed of. This different manner of use, taken in conjunction with the characteristics of processing blood, presents problems which are not addressed in the prior art. Blood is different from many other fluids which are processed in that it can and usually does change its characteristics in the course of processing, particularly because of blood's capability to clot. To this end the autotransfuser of this invention employs one or more defoaming elements placed in the path of blood being collected in a chamber. These elements protect the valved outlet from jamming, which is particularly important. An outlet valve which is jammed open such as by clotted blood or other debris allows the possibility of introducing bubbles or other debris into the patient's bloodstream which, as can be readily understood, is to be avoided.

Furthermore, many valves used in prior art devices are arranged to close by force of gravity. This, taken in conjunction with the concomitant requirement that the float elements float when sufficient fluid is collected, can result in a valve whose closure force is extremely small. We have found that this closure force (which is typically a function of gravity and hence the weight of the float) in many prior art devices was less than one gram, in some cases substantially less than one gram. The float valve in accordance with the autotransfuser of this invention employs a closure force (a weight) of the float valve which is substantially in excess of one gram, preferably in excess of five grams, and in a preferred embodiment on the order of ten grams. In order to ensure that the float valve also will float in blood, its specific gravity should be on the order of or slightly less than that of blood. In accordance with the preferred embodiment, we employ a blown form of a bloodcompatible material as the float element with a weight on the order of ten grams and which floats in blood. The float itself has a sealing member positioned so as to actually form a seal with a valve inlet when the fluid level drops below a minimum threshold. In a preferred embodiment the sealing membrane is silicone. Accordingly, the invention provides, in one aspect an autotransfusing device comprising:

a pair of blood collecting and reinfusing chambers each with rigid walls, each chamber including a blood inlet, a blood outlet and air inlet means including at least an air inlet, all said inlets and outlets of a chamber located in a substantially planar wall;

rotatable channelled means operatively associated with each of said chambers and rotatable relative thereto, said rotatable channelled means including a channel and a port for each of blood collection and blood infusion functions as well as a channel and a port for a vacuum source and an air channel;

said blood collection channel having an inlet coupled to said blood collection port and at least one blood collection channel end;

said blood infusion channel having an outlet coupled to said blood infusion port and at least one blood infusion channel end;

said vacuum channel coupled at one end to said vacuum port and having, in addition, at least one vacuum channel end;

said air channel coupled at one end to said air port and having, in addition, at least one air channel end;

said channel ends located in said rotatable channelled means so that with said rotatable channelled means in one position an air inlet and blood inlet of a first of said chambers coordinate in space with a vacuum channel end and a blood collection end, respectively; and a blood infusion channel end and an air channel end coordinate in space with an air inlet and said blood outlet, respectively of a second of said chambers.

With respect to another aspect, the invention provides an autotransfusing device comprising:

a pair of blood collecting and reinfusing chambers each with rigid walls, each chamber including a blood inlet, a blood outlet, a vacuum inlet and an air inlet, all said inlets and outlets of a chamber located in a first wall, first walls of both said chambers substantially coplanar with each other;

a rotatable disk supported for rotation adjacent said first walls of said chambers, said disk including a blood collection channel and a blood collection port, a blood infusion channel and a blood infusion port, as well as a port and a channel for a vacuum source and an air channel;

said blood collection channel having an inlet coupled to said blood collection port and at least one blood collection channel end;

said blood infusion channel having an outlet coupled to said blood infusion port and at least one blood infusion channel end;

said vacuum channel coupled at one end to said vacuum port and having, in addition, at least one vacuum channel end;

said air channel coupled at one end to said air source port and having, in addition, at least one air channel end;

said channel ends located in said disk so that with said disk in one position a vacuum inlet and blood inlet of a first of said chambers coordinate in space with a vacuum channel end and a blood collection channel end and a blood infusion channel end and an air channel end coordinate in space with an air inlet and a blood outlet of a second of said chambers.

BRIEF DESCRIPTION OF THE DRAWINGS

The invention will be further described in the following portions of this specification when taken in conjunction with the attached drawings in which like reference characters identify identical apparatus and in which:

FIGS. 1-6 relate to a first embodiment wherein:

FIG. 1 is an isometric illustration of a first embodiment of the invention;

FIG. 2 is a cross-section of the device shown in FIG. 1 illustrating the two chambers;

FIG. 3 is a cross-section of the device shown in FIG. 1 through the interior dividing wall and thus illustrating a single one of the two chambers;

FIGS. 4-6 illustrate the disk like device in three different positions, wherein FIG. 4 represents the disk like device in an inoperative or off position, FIG. 5 represents the disk like device in one operative position and FIG. 6 represents the disk like device in a second operative position;

FIGS. 7-10 relate to a second embodiment of the invention wherein FIGS. 7 and 8 represent the disk like device in first and second positions, respectively, each figure representing the relationship of major components of the disk like device to operative components of the receptacle;

FIG. 9 is an isometric view of the receptacle which cooperates with the disk like device shown in FIGS. 7 and 8;

FIG. 10 is a cross-section of the disk like device in accordance with a second embodiment of the invention;

FIGS. 11-16 relate to a third embodiment, wherein:

FIG. 11 is an assembly view of a preferred embodiment;

FIG. 12 is a cross-section of the device of FIG. 11 illustrating the two chambers;

FIG. 13 is a cross-section of the device of FIG. 11 through the interior dividing wall to illustrate a single one of the chambers;

FIGS. 14A-E are, respectively, bottom, top, section, section and details views of the chamber bulkhead of the preferred embodiment;

FIGS. 15A-D are, respectively, bottom, top, section and section views of the disk-like device or valve manifold of the preferred embodiment; and FIG. 16 is an exploded view of a preferred embodiment.

DETAILED DESCRIPTION OF PREFERRED EMBODIMENTS

Figure 1:
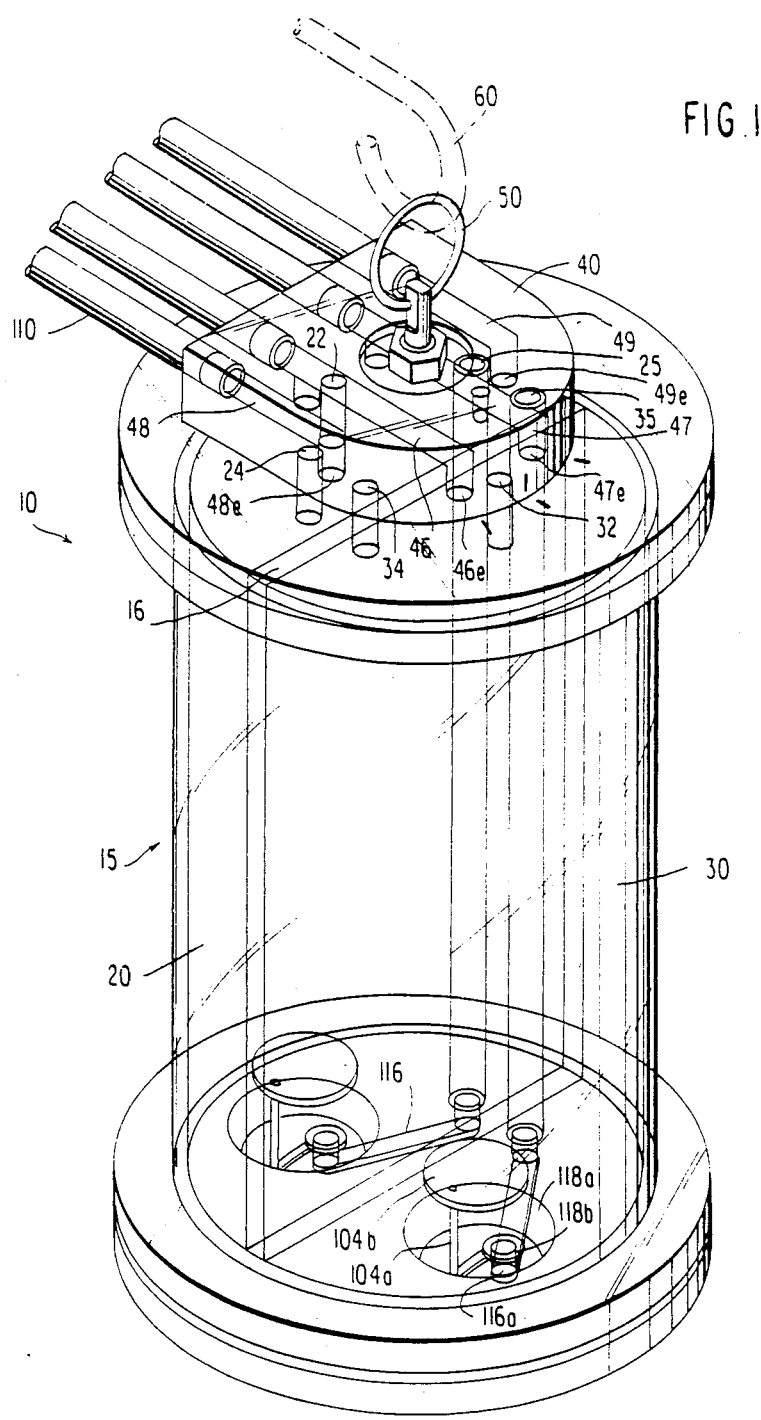
Figure 2:
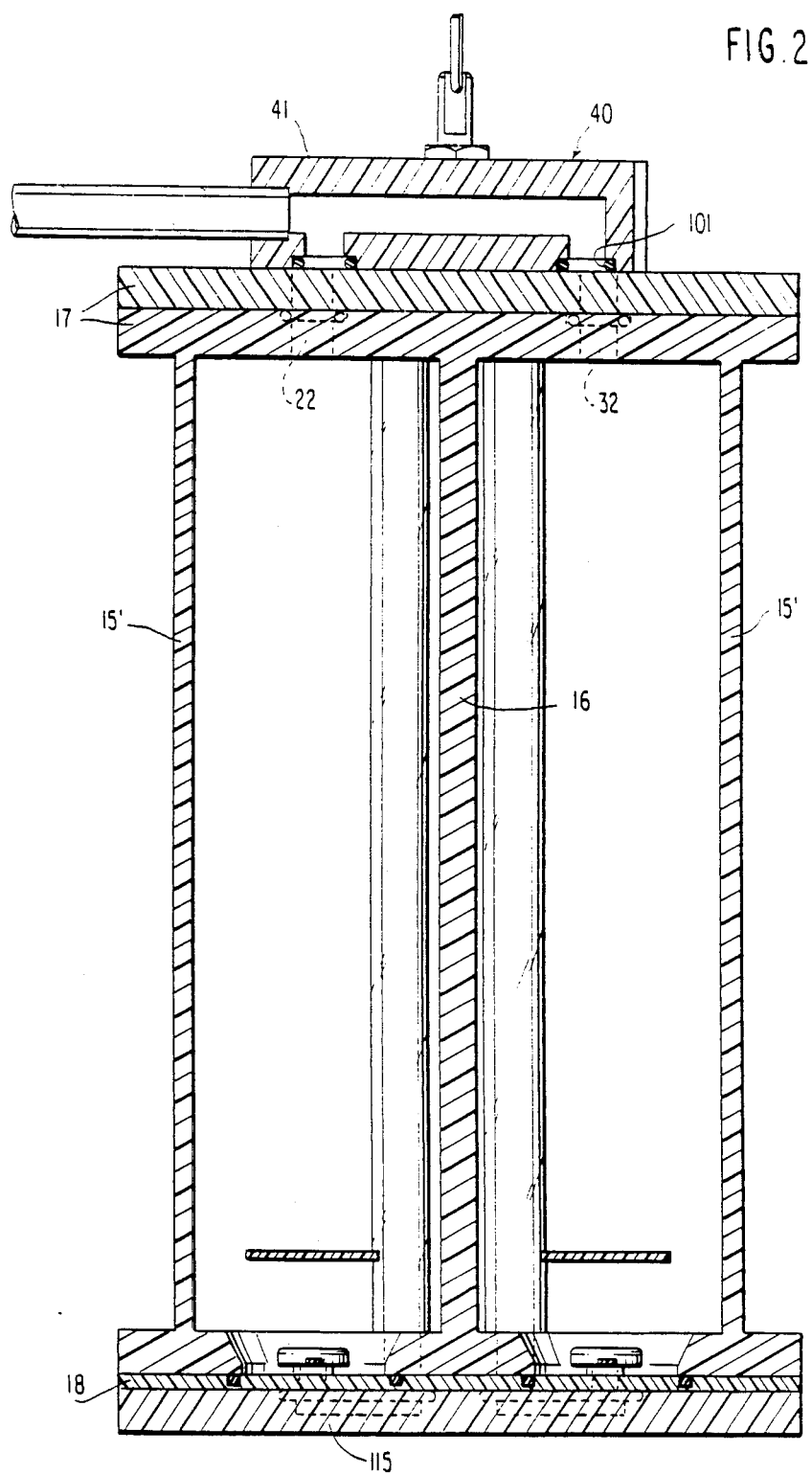
Figure 3:
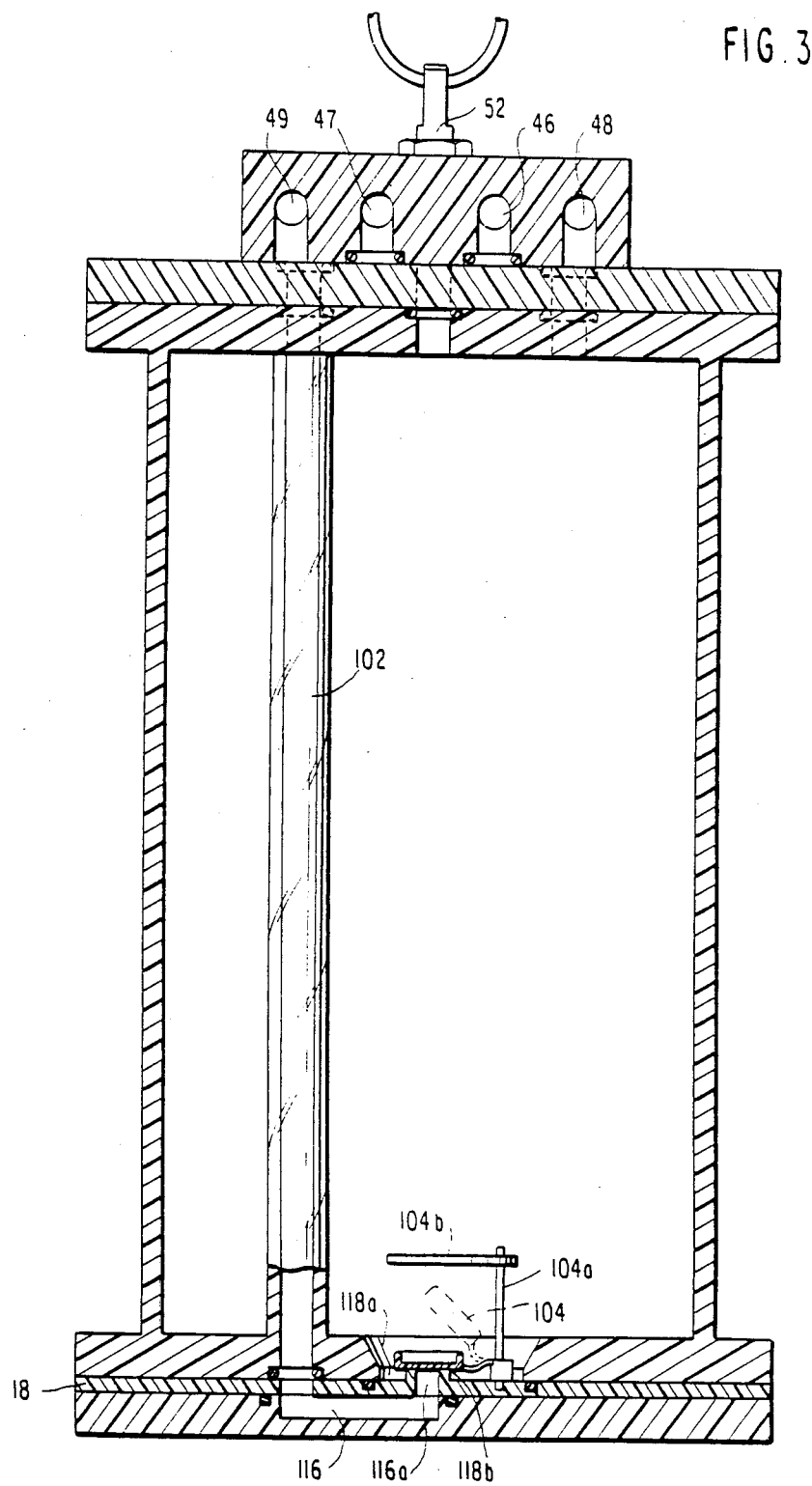

FIG. 1 is an isometric view of the first embodiment of an autotransfusing device in accordance with the invention. The autotransfuser 10 shown in FIG. 1 includes two major components, a receptacle 15 which includes a first chamber 20 and a second, entirely separate chamber 30 separated by a common wall 16. The exterior cylinder partially defining the receptacle 15, as illustrated in FIG. 1, is transparent. It should be apparent that a receptacle with transparent walls while preferable is not essential to the invention. However, it has the advantage of illustrating the internal details of the respective chambers. Associated with the receptacle 15 is the second major component, a disk like device 40 which is mounted for rotation relative to the receptacle 15. The support 50, in the form of a ring, is also fixedly mounted for supporting the disk like device 40 and the receptacle 15 from a support 60 such as is typically found in surgical theaters. The disk like device 40 as shown in FIG. 1 is also made of a transparent material, and it will be apparent to those skilled in the art that while preferable, this construction is not essential. FIG. 2 is a cross-section of FIG. 1 which cuts the dividing wall 16 between the chambers 20 and 30 of the receptacle 15, while FIG. 3 is a different section showing a typical chamber. As seen in FIGS. 1-3, the receptacle 15 includes a cylindrical side wall 15', and the chambers 20 and 30 are defined by a common wall 16 extending generally parallel to a longitudinal axis of the cylindrical side wall 15'. The receptacle has a bottom 115, and each chamber has a bottom wall 18 located within the receptacle 15. Each of the chambers 20 and 30 includes a top wall 17 which also forms the top of the receptacle 15. Located atop the wall 17 and mounted for rotation relative to the receptacle 15 is the disk like device 40. The disk like device 40 can rotate about a shaft 52 fixed to the receptacle 15 and is retained thereon by a retaining clip 51. The disk like device 40 includes a cover 41; as will be described, the main function of the disk like device 40 is that of a valve manifold. Each of the chambers 20 and 30 has a plurality of inlets and outlets, for example FIG. 2 shows that chamber 20 has an air inlet 22 and chamber 30 has an air inlet 32. The disk like device 40 includes four channels (see FIGS. 4-6), a blood inlet channel 48, a blood outlet or infusion channel 49, a vacuum channel 46 and a pressure channel 47. Each channel has a port at one end which tubing such as the tubing 110 can be connected thereto and one or more channel ends, opposite to the port. To provide a seal between the channel ends in the disk like device 40 and the inlets/outlets of the chambers 20 and 30 a plurality of seals such as O-rings 101 are provided; an O-ring 101 is provided adjacent each channel end for sealing the interface between the channel end and an appropriate inlet/outlet. Each chamber outlet (the blood outlet 25 of chamber 20 and the blood outlet 35 of chamber 30) is coupled by a respective pipe 102 to a valved flow path 116.

Reference is now made to FIG. 3 which is also a cross-section of FIG. 1, however, taken through the dividing wall 16 such that FIG. 3 is a cross-section of either chamber 20 or 30. Many of the elements already described are shown in FIG. 3, however, FIG. 3 shows the blood outlet path 116 from the chamber adjacent a float 104 and through the piping 102 up to the blood outlet, such as the outlet 25. More particularly, the bottom wall (of either chamber 20 or 30) includes a recess 118a providing a region for a blood pool. The recess 118a includes a valve seat 118b. A float 104, pivoted for hinged movement via a flexible arm 104c may be received in the valve seat 118b if the fluid level in the pool of recess 118a is reduced. When float 104 is received in seat 118b a valved flow path 116 is blocked. On the other hand, if the fluid level is high enough, the float 104 rises opening the flow path 116. The seat 118b has an opening communicating with an inlet 116a of the flow path 116. The flow path 116 communicates with the pipe 102 to the blood outlet 25 (of chamber 20) or 35 (of chamber 30). A canopy formed by vertical 104a and horizontal 104b may be used (either alone or along with a mesh element supported by elements 104a and 104b) to prevent clotted blood from passing into the path 116.

It will be appreciated from the foregoing that in order for a chamber such as chamber 20 to perform a blood collection function, two connections must be made, first a connection from a blood aspirating wand (or more particularly from the tubing 110 coupled thereto) to a blood inlet for the chamber 20 (blood inlet 24) and simultaneously a connection between the vacuum source (or more particularly the tubing 110 coupled to the vacuum source) and an air inlet for the chamber 20 such as the air inlet 22. When these connections are made, the vacuum drawn on the chamber 20 will drive the blood aspiration to draw blood into the chamber 20.

Likewise for a chamber such as the chamber 30, to perform a blood infusion function, two connections, albeit different connections, must be made. More particularly, there must be a connection between the blood outlet of the chamber 30, e.g. blood outlet 35 to the patient, or more particularly the tubing 110 coupled to the patient's catheter. At the same time, a connection must be made between a pressure source, or more particularly the tubing 110 coupled to the pressure bulb, to the air inlet for the chamber 30, e.g. air inlet 32. Since, in this embodiment, blood being infused is drawn from the bottom of the chamber and flows up the pipe 102, the chamber must be pressurized via the pressure source (not illustrated).

When the chamber 20 performs a blood infusion function, connections such as those described for chamber 30 must be made with respect to chamber 20. Likewise, when chamber 30 performs a blood collection function, connections must be made to chamber 30 such as those described for chamber 20, above.

The disk like device 40 is in effect a valve manifold and performs all of these functions in a manner now to be described.

The disk 40 has a first position (see FIG. 5) in which chamber 20 is enabled to perform a blood collection function and simultaneously chamber 30 is enabled to perform a blood infusion function. The disk 40 has a second position (see FIG. 6) wherein the chamber 20 performs a blood infusion function and simultaneously the chamber 30 performs a blood collection function. In other positions the valve manifold disables all connections.

Figure 4:
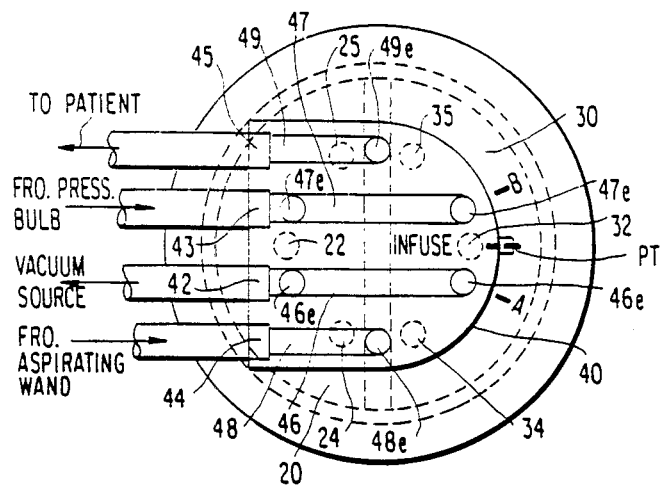
Figure 5:
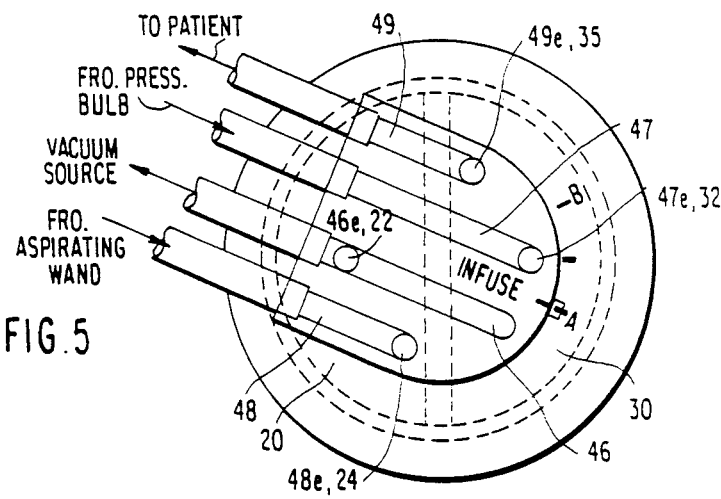
Figure 6:
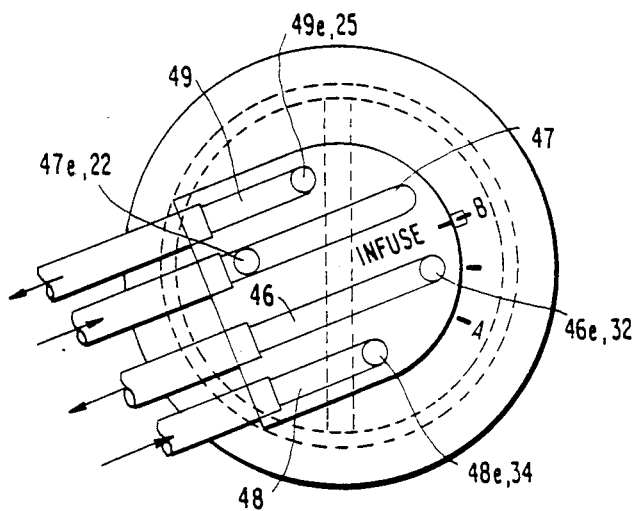

FIGS. 4-6 are top views of the autotransfuser 10 with the disk like device in an off position (FIG. 4), a first operative position (FIG. 5) and a second operative position (FIG. 6). In order to orient the reader, reference is first made to FIG. 4 to illustrate the components of the disk like device 40 and its cooperation with the receptacle 15 and the tubing 110. As shown in FIG. 4, the disk like device 40 includes four channels, a blood infusion channel 49, a pressure channel 47, a vacuum channel 46 and a blood inlet channel 48. The chamber 20 includes a blood outlet 25, a blood inlet 24 and an air inlet 22. Likewise, the chamber 30 includes a blood outlet 35, a blood inlet 34 and an air inlet 32. Each channel includes a port, such as a blood infusion port 45, a pressure port 43, a vacuum port 42 and a blood inlet port 44. Each port provides a coupling region for coupling to an end of appropriate tubing 110. As shown in FIG. 4 the tubing 110 coupled to the blood infusion port 45 is connected to a patient catheter. The tubing 110 coupled to the pressure port 43 is coupled to a pressure bulb, or any other convenient pressure source. The vacuum port 42 provides a region for connecting to tubing 110 coupled to a vacuum source and finally the blood inlet port 44 provides a region for connecting tubing coupled to an aspirating wand.

Each channel has at least one channel end, some channels have two channel ends. As shown in FIG. 4, the infusion channel 49 has a single channel end 49e, the blood inlet channel 48 has a single channel end 48e. On the other hand, pressure channel 47 has two channel ends 47e. Likewise the vacuum of the chambers 20 and 30 (22, 24, 25, 32, 34 and 35) as well as the channel ends 46e, 47e, 48e and 49e are located relative to each other so that selected connections are made between different channel ends and inlets and outlets with the disk in either of its two operative positions and on the other hand no connections are made with the disk in its inoperative or off position. As used herein, "making a connection" means that the respective inlet or outlet coordinates in space with a respective channel end. FIG. 4 shows the disk 40 in an inoperative or off position. To assist the user, the wall 17 has imprinted thereon indicia A and B, and the disk device 40 has a pointer PT. When the disk device 40 is located such that the pointer PT is adjacent the indicia A, then chamber 20 may perform a blood collection function and chamber 30 performs a blood infusion function. When the pointer PT is adjacent the indicia B, then chamber 30 may perform a blood collection function and chamber 20 performs a blood infusion function FIG. 5 shows the disk like device 40 in a first operative position wherein the chamber 30 performs a blood infusion function. With the disk like device 40 in the position shown in FIG. 5, the channel end 49e coordinates in space with the blood outlet 35 and simultaneously the channel end 47e coordinates in space with the air inlet 32. This spatial coordination allows pressure to communicate from the pressure bulb via the tubing 110, the pressure channel 47 through its end 47e, through the air inlet 32 into the chamber 30 for the purpose of pressurizing the chamber. As a result of that pressure, blood flows from blood path 116 (assuming a sufficient fluid level to remove float 104 from seat 118b), the pipe 102, the blood outlet 35 through the channel end 49e through the channel 49, the port 45 via the tubing 110 to the patient catheter. The other channel end 46e, located above chamber 30, is sealed by the upper surface of the wall 17 and the associated seal such as O-rings 101.

With the disk like device 40 in the position shown in FIG. 5, the chamber 20 performs a blood collection function via a similar coordination in space between inlets and outlets in the chamber 20 and the other channel ends. More particularly, the channel end 46e coordinates in space with the air inlet 22 so that vacuum is drawn on the chamber 20. At the same time, the channel end 48e coordinates in space with the blood inlet 24 and as a result blood is induced to flow from the aspirating wand via the tubing 110, the blood inlet port 44 through the blood inlet channel 48 via its end 48e, the blood inlet 24 into the chamber 20.

FIG. 6 shows the disk device in its other operative position. The reader can verify that it the position of FIG. 6 chamber 20 may perform blood infusion and chamber 30 may perform blood collection.

In the embodiment of the invention just described, each chamber included three inlet/outlets, a blood inlet, a blood outlet and an air inlet. The air inlet performed a dual function in that with the disk 40 in one operative position it provided communication via a vacuum channel to a source of a vacuum, and with the disk device 40 in another operative position it provided communication to a pressure source. However, as will be described hereinafter, that is not essential to the invention and in a second embodiment of the invention to be described in connection with FIGS. 7-10, each chamber includes four inlet/outlets. The second embodiment has, in addition to the blood inlet and blood outlet, and in lieu of the air inlet, a vacuum inlet and a distinct pressure inlet. The disk like device of the second embodiment has the same dual ended pressure and vacuum channels as does the first embodiment but also has dual ended infusion and collection channels.

Figure 8:
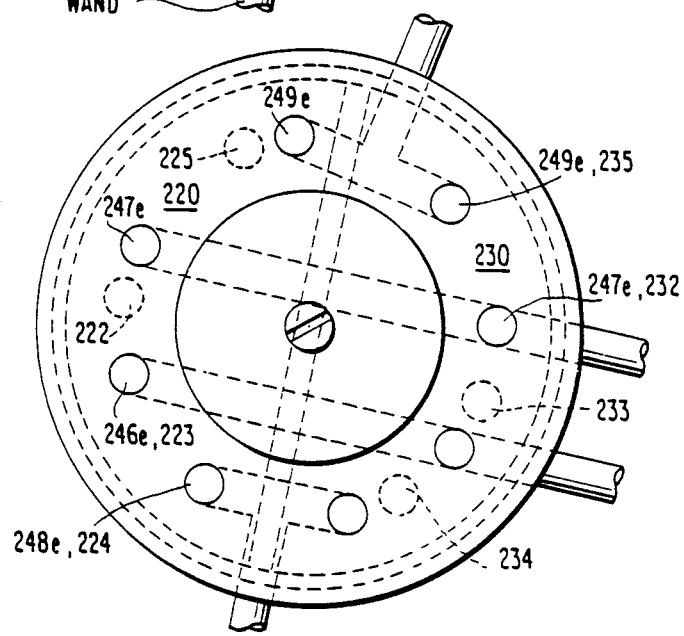
Figure 9:
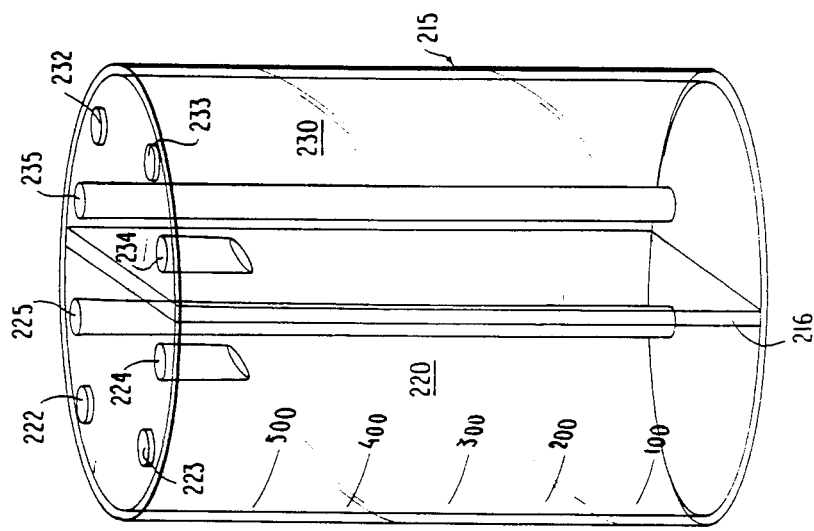

FIG. 9 shows the receptacle 215 of the second embodiment. The receptacle 215 includes a cylindrical outer wall which is divided into chambers 220 and 230 by an interior common wall 216. As shown in FIG. 9 each of the chambers 220 and 230 has four inlets/outlets, blood inlets 224, 234, blood outlets 225, 235, pressure inlets 222 and 232 and vacuum inlets 223 and 233. As will be described in connection with FIGS. 7 and 8, a valve manifold comprising a disk like device 240 is mounted rotatably relative to the receptacle 215. The disk like device 240 has a plurality of channels, each channel having ends which are positioned so that they coordinate in space selectively with the inlets/outlets of the chambers 220 and 230 to alternately perform the infusion and collection functions.

Figure 7:
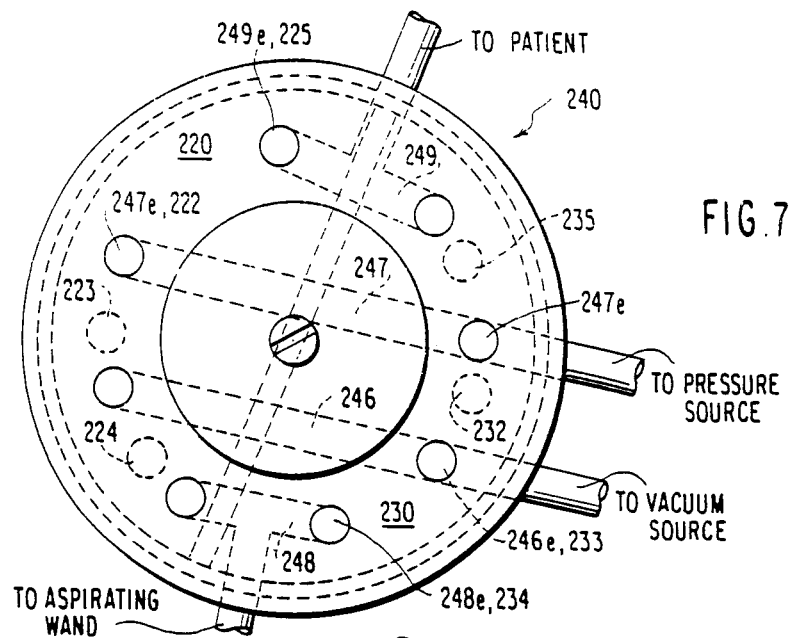

FIGS. 7 and 8 are top views of the disk like device or manifold in two different operative positions. In each figure the relationship between the channel and channel ends and the chamber inlet/outlets is made explicit by showing closed inlet/outlets in dotted fashion.

FIG. 7 illustrates the state wherein the chamber 230 is performing a blood collection function and the chamber 220 is performing a blood infusion function. Thus, for example, the blood collection channel 248 has a channel end 248e overlying the blood inlet 234 of the chamber 230. Likewise, the vacuum channel 246 has a channel end 246e which coordinates in space with the vacuum inlet 233 of the chamber 230. The pressure inlet 232 and the blood outlet 235 of the chamber 230 are sealed by the fact that pressure channel end 247e does not coordinate in space with the pressure inlet 232 nor does the blood outlet 235 coordinate in space with the blood infusion channel end 249e. Those channel ends 248e and 246e adjacent the chamber 220 are sealed by the O-rings 101. Of course just the opposite condition is true with respect to the chamber 220, e.g. the blood inlet 224 and the vacuum inlet 223 are sealed whereas the pressure inlet 222 coordinates in space with the pressure channel end 247e and the blood outlet 225 coordinates in space with the blood outlet channel end 249e. The connections made with channel ends 247e and 249e adjacent chamber 230 are sealed by O-rings 101. FIG. 8 is just the reverse wherein the chamber 220 is performing a blood collection function and the chamber 230 is performing a blood infusion function.

Figure 10:
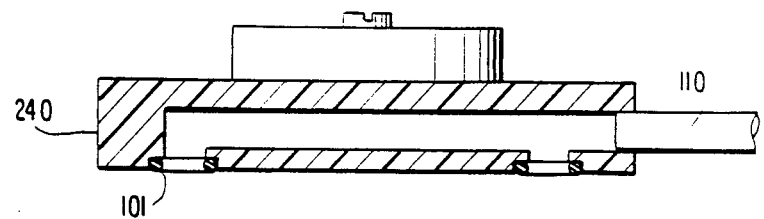

FIG. 10 is a cross-section of the valve-like device 240 which, as is shown in FIG. 10, is substantially similar to the valve-like device 40 of the first embodiment. FIG. 10 shows that channel ends which do not coordinate in space with an inlet or outlet are sealed.

In both of the embodiments thus far described the receptacle (encompassing both the chambers) is normally oriented vertically with the valve manifold or disk-like device at the "top". In a preferred embodiment, however, whereas the receptacle is also normally oriented vertically, the valve manifold or valve-like device is at the "bottom". A particular advantage of the preferred embodiment is that the blood paths (both blood collection and blood infusion) do not exhibit the right angle or 90° elbow which is a characteristic of the first and embodiments. More particularly, both FIGS. 2 and 10 show that in both embodiments the blood channels include a 90° turn; as will be described hereinafter, this is not true of the preferred embodiment which is illustrated in FIGS. 11-16. It will be apparent that the same advantage can be achieved with the valve manifold at the top rather than the bottom. One consequence of locating the valve manifold at the "bottom" is that there is now no longer a requirement for tubing (pipe 102) interior of a chamber to connect the blood outlet to an outlet valve; since the outlet valve, at the bottom of the chamber, is adjacent the blood outlet of the chamber. This allows the infusion to be driven by gravity and eliminates the requirement for a pressure source. On the other hand each chamber includes, in the preferred embodiment, two tubes which are not present in the first and second embodiments. One of these tubes is associated with the air inlet so as to allow vacuum or pressure or venting to be introduced at the "top" of the chamber. The other tube is associated with the blood inlet and conducts blood drawn into the chamber to enter at the >top for reasons described hereinafter. Further advantages of this architecture are that it allows an operator a better view of the position of the disk like device or valve manifold and it allows the connecting tubing 110 to be managed or positioned more readily.

Figure 11:
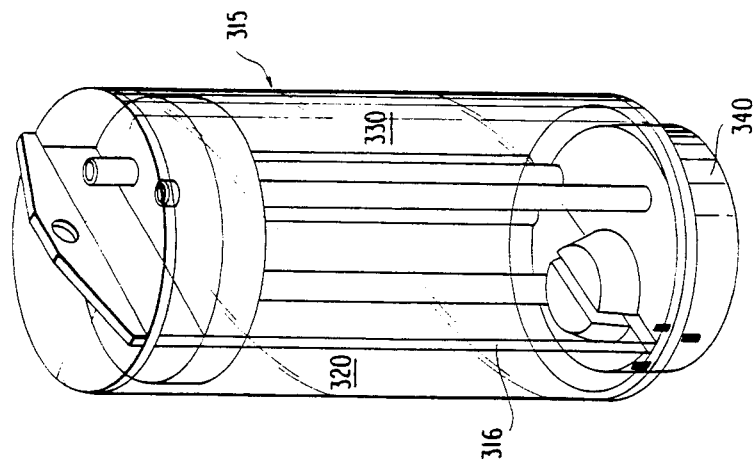

FIG. 11 is an assembly view showing of the auto-transfuser of the preferred embodiment showing the receptacle 315 including chambers 320 and 330 separated by a common wall 316. The valve manifold or disk-like device 340 is seen at the "bottom" where it can be coupled to tubing 110. In the preferred embodiment each chamber includes three inlets/outlets as in the first embodiment, that is, a blood inlet, a blood outlet and an air inlet (which alternately connects to a vacuum on the one hand and to ambient air or a pressure source on the other hand). The components of this preferred embodiment are more clearly seen in the exploded view of FIG. 16. As shown in FIG. 16 the cylindrical receptacle 315 is divided into two chambers by the common wall 316. A chamber bulkhead 350 comprises a chamber bulkhead base 351 and four upstanding tubes or pipes. A vacuum/pressure pipe 322 and a blood inlet pipe 323 are associated with the chamber 320 and correspondingly a vacuum/pressure pipe 332 and a blood inlet pipe 333 are associated with the chamber 330. Although the pressure source is optional in this embodiment, we shall refer to pressure channels and pipes with the understanding that this is not a suggestion that a pressure source is essential. Located adjacent the upper edge of each of these pipes is a blood defoaming element 321 (in chamber 320) and a blood defoaming element 331 (in chamber 330). Shelves 321a and 331a supported within chambers 320 and 330 in turn support the defoaming elements 321 and 331. Located near the base of the bulkhead 351, in the chamber 320, is a float 363 and a float frame 365. A similar float 364 and frame 366 are associated with the chamber 330. Below the bulkhead 351 is the disk like device 340. This includes a manifold cover 341 having six apertures therein for blood flowing in, blood flowing out and vacuum and pressure lines. More particularly, as will be explained below, a blood infusion channel end terminates at 349e and a blood inlet channel end terminates at 348e. Vacuum channel ends 346e and pressure channel ends 347e comprise the six operating passageways in the valve manifold 341. A central opening 358 provides a passageway for a threaded screw 352 on which is mounted the washer 353. The threaded screw 352 also passes through a hole 354 in a manifold plate 357 as well as the seal 355. The manifold plate includes a pressure (or vent) port 343 and a vacuum port 342. As will be described below, the pressure and vacuum derived from these ports is communicated in channels to the pressure channel ends 347e and the vacuum channel ends 346e. The canopies 361 and 362, when assembled, overlie the floars 363 and 364. A bulkhead seal 317 interfaces with a ridge 359 in the bulkhead base 351. The wall 316 fits into a recess 359a formed between parallel portions of the ridge 359.

FIG. 15A is a bottom view of the valve manifold 341. As seen in FIG. 15A, the valve manifold 341 includes a plurality of apertures, a central aperture 358 for mounting purposes, a blood inlet port 344 and a blood infusion port 345. The manifold 341 also includes depressions corresponding to a vacuum channel 347 and a pressure channel 346. The depressions 347 and 346 cooperate with the manifold plate 357 (see FIG. 16) to form the vacuum channel 347 and the pressure channel 346. The tabs 337 and 338 are used for operator convenience as will be described. FIG. 15B is a top view of the valve manifold 341 showing the central aperture 358 as well as the six operating channel ends, the pressure channel ends 346e, the vacuum channel ends 347e, the blood inlet channel end 349e and the blood infusion channel end 348e. FIG. 15C is the section A—A which shows the pressure channel depression 346 and its ends 346e. Adjacent the pressure channel ends 346e are O-ring seal seats 101a. Similar seats are provided adj-cent the other channel ends as well. FIG. 15D is the section B—B (see FIG. 15A). This shows the blood inlet channel 349, the blood infusion channel 348, the vacuum channel 347 and the pressure channel 346 spaced apart from the central aperture 358. As seen in FIG. 15D, the blood inlet port 344 is opposite the channel end 349e. The blood infusion port 345 is opposite the channel end 348e of the blood infusion channel 348.

FIGS. 14A through E are various views of the chamber bulkhead 350. More particularly, FIG. 14A is a bottom view of the chamber bulkhead having a plurality of apertures matching the apertures in the valve manifold 341 (see FIG. 15B). More particularly, the central aperture 458 is threaded to receive the screw 352. The bulkhead 351 cooperates with the receptacle 315 and the common wall 316 to define chambers 320 and 330 (see FIG. 11). The recess 359a serves to locate the common wall 316. As shown in FIG. 14A, the bulkhead provides for three apertures for each chamber. A first chamber includes a blood inlet 383, a blood outlet 385 and an air inlet 382 (which, as in the first embodiment, alternately provides for vacuum or pressure). Similarly, the other chamber includes a blood inlet 393, a blood outlet 395 and an air inlet 392. In the top view (FIG. 14B) the air inlet 392 communicates with the vacuum/pressure pipe 332 and similarly the air inlet 382 communicates with the vacuum/pressure pipe 322. The blood inlet 393 communicates with the blood inlet pipe 333 and the blood inlet 383 communicates with the blood inlet pipe 323. The blood outlets 395 and 385 communicate respectively, on the other side of the bulkhead 351, with blood outlet apertures 335 and 325. Adjacent these apertures are posts 326 and 336 for mounting the hinged float 363 and 364, respectively. Each of these floats includes frame 365 and 366 for purposes which will be described hereinafter. FIG. 14E is a detail of the region within the dotted circle in FIG. 14D.

When the components (see in particular FIG. 16) are assembled, the manifold plate 357, seal 355 and valve manifold 341 provide the same four channels, each with a port and at least one channel end as in the first and second embodiments. More particularly, the manifold plate 357 cooperates with the depressions 346 and 347 in the valve manifold 341 to form the vacuum channel 346 and pressure channel 347, respectively. FIG. 15C is a typical section showing the vacuum channel with its channel ends 346e. Pressure channel 347 is completely similar. FIG. 15D shows the blood inlet channel 348 with its port 345 at one end and its channel end 348e at the other end. The blood infusion channel 349 has an infusion port 344 at one end and a channel end 349e at the other end. With the valve manifold rotated to one operative position, the blood inlet channel end 348e communicates with either the blood inlet 383 or 393. The location of the vacuum ends 346e is arranged to simultaneously communicate with the air inlet either 382 or 392 so that the chamber is provided both with a blood inlet flow path and a vacuum. By the same token, the blood outlet channel end 349e coordinates in space either with the blood outlet end 395 or 385 of the corresponding chamber so as to simultaneously form an outlet path for blood stored in the chamber and a pressure source (or vent) to drive (or allow flow of) the blood out of the chamber. The adjacent surfaces of the valve manifold 341 and the lower surface of the chamber bulkhead 351 provide for sealing for those apertures which do not coordinate in space with apertures in the other element. In other words, regardless of which function is performed by which chamber, there is a pressure channel end 347e and a vacuum channel end 346e which are not involved in a connection. Those ends are sealed by the lower surface of the bulkhead 351 and the seals mounted in the valve manifold 341 adjacent the respective channel ends. Similarly, when the valve manifold is in an inoperative position wherein no connections are made, then of course all pressure channel ends 347e and all vacuum channel ends 346e are sealed in a similar fashion. When the valve manifold is in an inoperative position, in addition to the foregoing sealing, the chamber blood outlets 395 and 385 are sealed against a surface of the valve manifold 341 through the cooperation of the adjacent seals 101 and the larger seals 401 (see FIG. 16).

It should be apparent from the foregoing that by simply rotating the valve manifold (by grasping the tabs 337, 338) through 45° (in an embodiment which has actually been constructed the function of the chambers can be altered between infusion and collection and vice versa.

Figure 12:
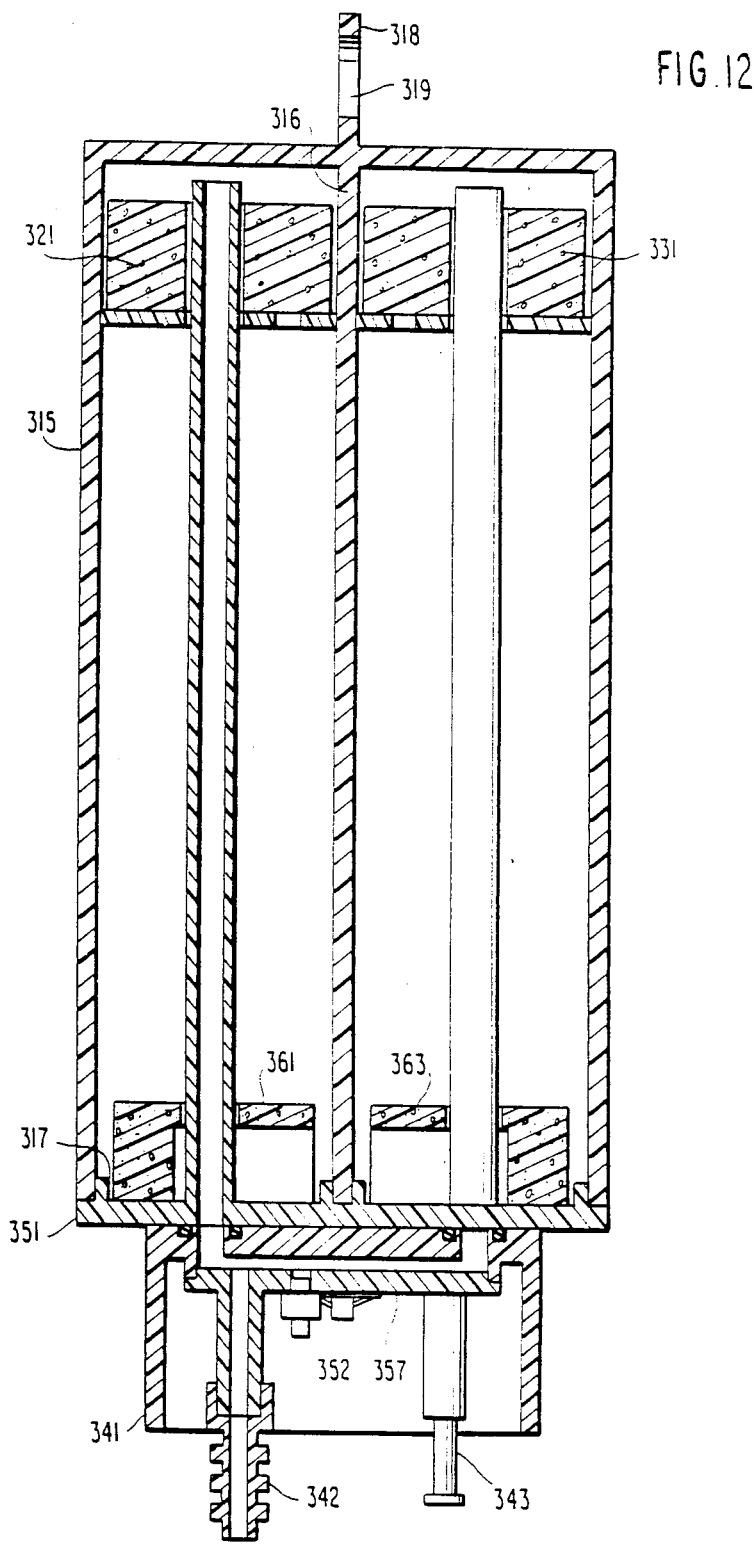
Figure 13:
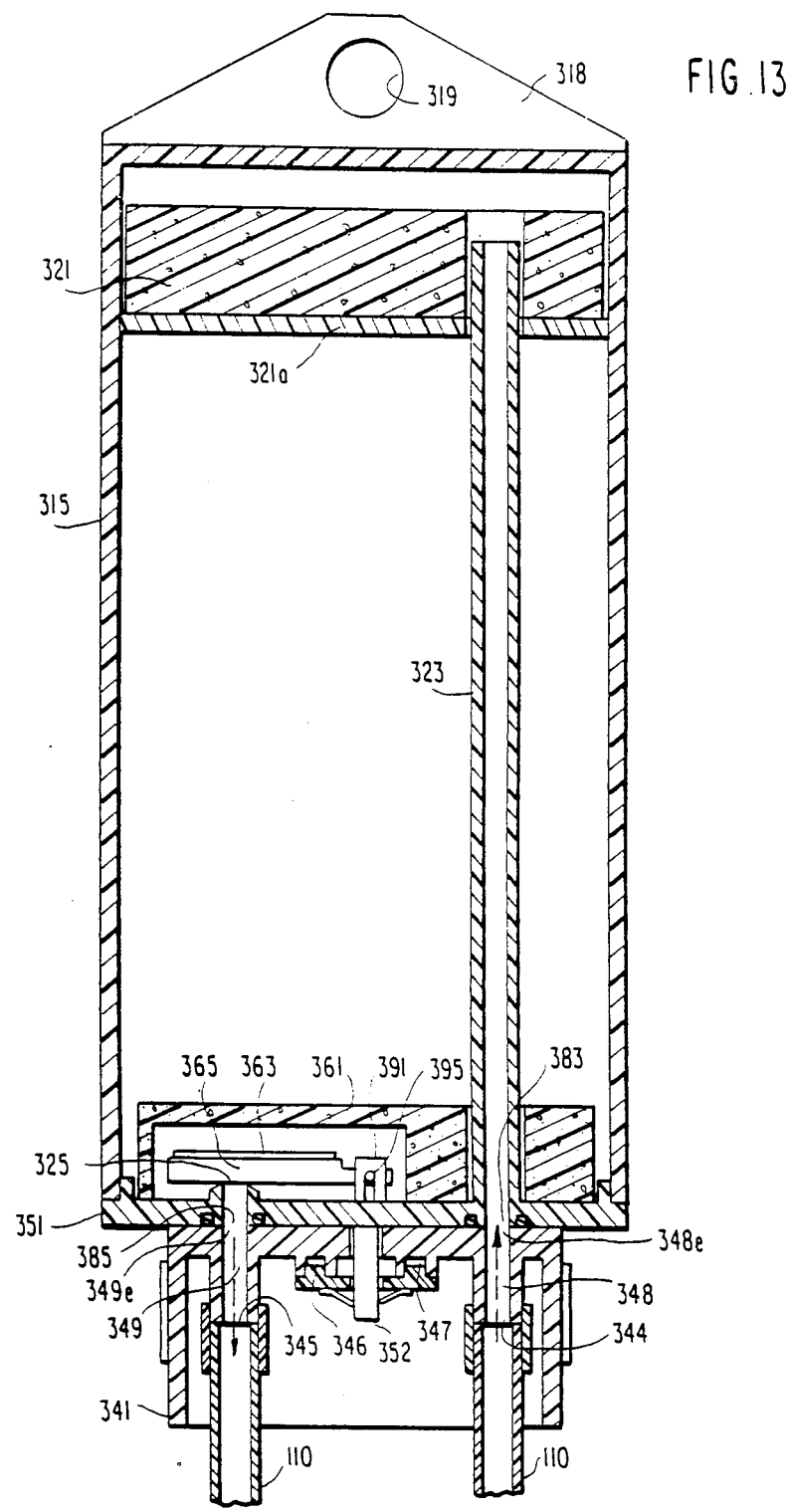

Many of the same elements already described are seen in the cross-sections of FIGS. 12 and 13; however these views illustrate other features of the ivention.

More particularly, and referring to FIG. 13, the defoaming element 321 and its relationship to the blood inlet pipe 323 is illustrated. The dotted arrows show a blood inlet path through tubing 110, the blood inlet port 344, the blood inlet channel 348, the blood inlet channel end 348e, the inlet 383 and the pipe 323.

A typical blood infusion path, is also shown. It should be noted that FIG. 13 does not explicitly represent the fluid level although by the position of the float 363 the fluid level is assumed to be sufficiently high to displace the float from the valve seat. Thus blood can flow through the filter element or canopy 361, through the blood outlet aperture 325, the blood outlet end 385, the infusion channel end 349e, the channel 349 and the port 345.

FIG. 12, being a different section shows, on the other hand, the vacuum port 342 and the pressure port 343.

A model of the third embodiment has actually been implemented. In practice we contemplate that the receptacle 15 will be injection molded polycarbonate as the chamber bulkhead 350, the valve manifold 341 and the manifold top plate 357. The seals 317 and 355 are assembled as shown in FIG. 16 and the entire structure is subjected to RF energy to melt the seals 317 and 355 to unite adjacent elements in accordance with the EMAWELD process. The defoaming elements 321 and 331 will be dye cut open cell urethane foam, as will the protective canopies 361 and 362. The float valves 363, 365 will be a suttable blood-compatible material supporting silicone membranes. Suitable materials are polypropylene, polyethelene or polycarbonate. The former two have an advantage in terms of density. The seals 101 will be silicone. The screw 352 and washer 353 will be stainless steel, although other conventional fasteners could be used. As has been indicated above, in the course of building and testing several models of different embodiments of the invention, we have found that signficant improvements can be made in the float valve, which is used at the blood outlet of the autotransfuser. Prior art autotransfusers employed float valves to perform this function. In order for the valve to float, of course the specific gravity of the float element had to be equal to or less than the specific gravity of blood. The closure force which was exerted, as the blood level decreased, is of course induced by gravity and is thus a function of the weight of the float. Most prior art float valves for blood flow used floats which weighed on the order of one gram and more typically, substantially less than a gram. As is also indicated above, processing blood must take into account the characteristics of blood which are distinctly different from most other fluids. One significant difference is the ability, and actual affinity, of blood to clot when it comes into contact with man-made surfaces. Even if blood clotting is retarded, by the use of blood compatible components (such as polycarbonate, stainless steel, etc.), some clotting does occur. If the float valve has a small closure force (a gram or less than a gram) it is distinctly possible for the float to "stick" on either a partially formed blood clot or other debris. Disasterous consequences can obviously flow from a "stuck" float valve. To remedy this problem, we have sought to significantly increase the closure force of such a float valve. In order to ensure that the float still has the ability to "float" in a pool of blood, the specific gravity of the valve (notwithstanding its increased weight) must still be equal to or less than that of blood. We have found firstly that blown forms of suitable materials can be made with the required specific gravity and can also be fashioned into a float whose weight is significantly above a gram, preferably above five grams and in an embodiment which we intend to build, about ten grams. Such a float 363 is shown in FIG. 16. The float itself includes a frame 365 on which is mounted a sealing membrane (silicone) 390. The float frame 365 includes a pin 395 which is rotatably received within the bracket 391 secured to the bulkhead base 351. Because of the weight of the float 363 (about ten grams), as the blood level in a chamber decreases, the closure force exerted on the valve is about ten grams and is sufficient to provide reliable closure, notwithstanding partially formed blood clots or other debris.

It should be apparent from the foregoing that the invention provides a simple to manufacture, readily assembled and simple to use autotransfuser. While several specific embodiments of the invention have been described, it should be apparent that many changes can be made without departing from the spirit and scope of the invention which is to be construed in accordance with the claims attached hereto and is not to be limited by the descriptive examples provided hereinabove.

We claim:

1. An autotransfusing device comprising:
    a pair of blood collecting and reinfusing chambers each with rigid walls, each chamber including a blood inlet, a blood outlet and air inlet means including at least an air inlet, all said inlets and outlets of a chamber located in a substantially planar wall;
    rotatable channeled means operatively associated with each of said chambers and rotatable relative thereto, said rotatable channeled means including a channel and a port for each of blood collection and blood infusion functions as well as a channel and a port for a vacuum source and an air channel;
    said blood collection channel having a inlet coupled to said blood collection port and at least one blood collection channel end;
    said blood infusion channel having an outlet coupled to said blood infusion port and at least one blood infusion channel end;
    said vacuum channel coupled at one end to said vacuum port and having, in addition at least one vacuum channel end;
    said air channel coupled at one end to said air port and having, in addition at least one air channel end;
    said channel ends are located in said rotatable channeled means so that with said rotatable channeled means in one operative position an air inlet and blood inlet of a first of said chambers coordinate in space with a vacuum channel end and a blood collection end, respectively; and
    a blood infusion end and an air channel end coordinate in space with an air inlet and said blood outlet, respectively of a second of said chambers.

2. An autotransfusing device as recited in claim 1 wherein:
    said channel ends located in said rotatable channeled means so that with said rotatable channeled means in a second operative position said air inlet and blood inlet of said second of said chambers coordinate in space with a vacuum channel end and a blood collection end, respectively; and
    a blood infusion end and an air channel end coordinate in space, respectively with an air inlet and said blood outlet of said first of said chambers.

3. An autotransfusing device as recited in claim 1 wherein said first and second chambers are formed in a unitary cylinder and each has a wall in common with the other.

4. An autotransfusing device as recited in claim 1 and further including:
    a valved outlet in each of said chambers, and piping means connecting said each said valved outlet to a respective blood outlet of the chamber.

5. An autotransfusing device as recited in claim 4 wherein said valved outlet of said chambers are located in a wall of the chamber which is substantially parallel to and spaced from said planar wall.

6. An autotransfusing device as recited in claim 1 further including seal means located between said rotatable channelled means and said chambers to provide an air tight coupling between inlets and outlets of said chambers and said channel ends when said channel ends and said inlets and outlets coordinate in space.

7. An autotransfusing device as recited in claim 1 which further includes:
    a valved outlet in each of said chambers, said valved outlet including a pivoted float with a weight of at least 5 grams.

8. An autotransfusing device as recited in claim 7 wherein said float has a silicone sealing membrane.

9. An autotransfusing device as recited in claim 1 wherein said air inlet means includes a vacuum inlet and a separate pressure inlet and wherein in said one position of said rotatable channeled means a vacuum channel end coordinates in space with said vacuum inlet of one of said chambers and an air channel end coordinates in space with an air inlet of said second said chambers.

10. An autotransfusing device comprising:
    a pair of blood collecting and reinfusing chambers each with rigid walls, each chamber including a blood inlet, a blood outlet, a vacuum inlet and an air inlet all said inlets and outlets of a chamber located in a first wall, said first walls of said chambers substantially coplanar with each other;
    a rotatable disk supported for rotation adjacent said first walls of said chambers, said disk including a blood collection channel and a blood collection port, a blood infusion channel and a blood infusion port as well as a port and a channel for a vacuum source and an air channel;
    said blood collection channel having a inlet coupled to said blood collection port and at least one blood collection channel end;

said blood infusion channel having an outlet coupled to said blood infusion port and at least one blood infusion channel end;

said vacuum channel coupled at one end to said vacuum port and having, in addition at least one vacuum channel end;

said air channel coupled at one end to said air channel port and having, in addition at least one air channel end;

said channel ends located in said disk so that with said disk in one position a vacuum inlet and blood inlet of a first of said chambers coordinates in space with a vacuum channel end and a blood collection end and a blood infusion channel end and an air channel end coordinate in space with an air inlet and said blood outlet of a second of said chambers.

11. An autotransfusing device as recited in claim 12 wherein:

said channel ends are located in said rotatable disk so that with said disk in a second position a vacuum inlet and blood inlet of said second of said chambers coordinate in space with a vacuum channel end and a blood collection channel end, respectively; and a blood infusion channel end and an air channel end coordinate in space with an air inlet and said blood outlet, respectively of said first of said chambers.

12. An autotransfusing device as recited in claim 10 wherein said first and second chambers are formed in a cylinder and each has a wall in common with the other.

13. An autotransfusing device as recited in claim 10 and further including:

a valved outlet in each of said chambers, and piping means connecting each said valved outlet to a respective blood outlet of the chamber.

14. An autotransfusing device as recited in claim 13 wherein said valved outlet of said chambers are located in a wall of the chamber which is substantially parallel and spaced from said first wall.

15. An autotransfusing device as recited in claim 10 further including seal means located between said disk and said chambers to provide an air tight coupling between inlets and outlets of said chambers and said channel ends when said channel ends and said inlets and outlets coordinate in space.

16. An autotransfusing device comprising:

a pair of blood collecting and reinfusing chambers each with rigid walls, each chamber including a blood inlet, a blood outlet and an air inlet, all said inlets and outlets of a chamber located in a first wall, said first walls of said chambers substantially coplanar with each other;

a rotatable disk supported for rotation adjacent said first walls of said chambers, said disk including a blood collection channel and a blood collection port, a blood infusion channel and a blood infusion port as well as a port and a channel for a vacuum source and an air channel;

said blood collection channel having a inlet coupled to said blood collection port and at least one blood collection channel end;

said blood infusion channel having an outlet coupled to said blood infusion port and at least one blood infusion channel end;

said vacuum channel coupled at one end to said vacuum port and having, in addition at least one vacuum channel end;

said air channel coupled at one end to said air channel port and having, in addition at least one air channel end;

said channel ends located in said disk so that with said disk in one position an air inlet and blood inlet of a first of said chambers coordinate in space with a vacuum channel end and a blood collection channel end and a blood infusion channel end and an air channel end coordinate in space with an air inlet and said blood outlet of a second of said chambers.

17. An autotransfusing device as recited in claim 16 wherein:

said channel ends located in said rotatable disk so that with said disk in a second position an air inlet and blood inlet of said second of said chambers coordinate in space with a vacuum channel end and a blood collection channel end, respectively; and a blood infusion channel end and an air channel end coordinate in space with an air inlet and said blood outlet, respectively of said first of said chambers.

18. An autotransfusing device as recited in claim 16 wherein said first and second chambers are formed in a cylinder and each has a wall in common with the other.

19. An autotransfusing device as recited in claim 16 and further including:

a valved outlet in each of said chambers, and piping means connecting each said valved outlet to a respective blood outlet of the chamber.

20. An autotransfusing device as recited in claim 21 wherein said valved outlet of said chambers are located in a wall of the chamber which is substantially parallel to and spaced from said first wall.

21. An autotransfusing device as recited in claim 16 further including seal means located between said disk and said chambers to provide an air tight coupling between inlets and outlets of said chambers and said channel ends when said channel. ends and said inlets and outlets coordinate in space.

22. An autotransfusing device as recited in claim 16 which further includes:

a valved outlet in each of said chambers, said valved outlet including a pivoted float with a weight of at least 5 grams.

23. An autotransfusing device as recited in claim 24 wherein said float has a silicone membrane.

24. An autotransfusing device as recited in claim 16 which further includes in each chamber:

an upstanding pipe with an entrance end in communication with said blood inlet, said pipe having an outlet, a foam defoaming element located below said outlet of said pipe.

25. An autotransfusing device as recited in claim 24 which further includes, in each chamber:

a vacuum/pressure pipe with an entrance end in communication with said air inlet and an outlet, said outlet of said vacuum/pressure pipe located above said defoaming element.

26. An autotransfusing device as recited in claim 22 which further includes, in each chamber:

a filter element located above said float and said valved outlet.

27. An autotransfusing device as recited in claim 16 wherein said blood collection and infusion channels have longitudinal axes parallel to each other and said air and vacuum channels have longitudinal axes parallel to each other and wherein said axes of said blood collection and infusion channels are substantially perpendicular to said axes of said air and vacuum channels.

28. An autotransfusing device as recited in claim 16 wherein said rotatable disk includes:
- a cup shaped element with a base and a skirt, said base with a pair of parallel depressions,
- a plate secured to said cup shaped element, said plate having a pair of parallel channels forming said blood collection and infusion channels, said plate including means for separately enclosing said parallel depressions to form said air and vacuum channels, and
- means securing said plate to said cup shaped element.

29. An autotransfusing device as recited in claim 28 which further includes four upstanding tubes, two in each said chamber,
- a tube in each chamber having an entrance end for communication with a blood collection channel end and an outlet end,
- a tube in each channel having an entrance end for communication with either an air or vacuum channel end, and an outlet end,
- a defoaming element in each chamber located below said outlet ends of said tubes.

* * * * *